(12) United States Patent
Kuchimaru

(10) Patent No.: US 8,360,966 B2
(45) Date of Patent: Jan. 29, 2013

(54) LENS DRIVE CONTROL APPARATUS, LENS DRIVE APPARATUS AND ENDOSCOPE SYSTEM

(75) Inventor: Toru Kuchimaru, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 13/072,437

(22) Filed: Mar. 25, 2011

(65) Prior Publication Data

US 2011/0275897 A1 Nov. 10, 2011

Related U.S. Application Data

(63) Continuation of application No. PCT/JP2010/054660, filed on Mar. 18, 2010.

(30) Foreign Application Priority Data

Apr. 2, 2009 (JP) ................................. 2009-090396

(51) Int. Cl.
*A61B 1/06* (2006.01)
*A61B 1/00* (2006.01)
(52) U.S. Cl. ......................... 600/167; 600/129; 600/168
(58) Field of Classification Search .................. 600/118, 600/151, 167, 168, 173, 143, 160, 106; 348/345, 348/357, 369; 359/820, 823, 824; 396/93, 396/133; 60/527, 528
See application file for complete search history.

(56) References Cited

U.S. PATENT DOCUMENTS 6,939,338 B2 * 9/2005 Waldhauser et al. ......... 604/531
2007/0100209 A1 * 5/2007 Takahashi .................... 600/167
2007/0280668 A1 12/2007 Kubo et al.
2008/0247748 A1 * 10/2008 Tanimura et al. ............. 396/502

FOREIGN PATENT DOCUMENTS

| JP | 59-202426 | 11/1984 |
|---|---|---|
| JP | 07-264886 | 10/1995 |
| JP | 2003-207709 | 7/2003 |
| JP | 2007-004121 | 1/2007 |
| JP | 2008-020811 | 1/2008 |
| JP | 2008-194178 | 8/2008 |

OTHER PUBLICATIONS

International Search Report dated May 11, 2010.

* cited by examiner

*Primary Examiner* — Philip R Smith
*Assistant Examiner* — Rynae Boler
(74) *Attorney, Agent, or Firm* — Scully, Scott, Murphy & Presser, P.C.

(57) ABSTRACT

A lens drive control apparatus of the present invention controls a lens drive system that has a lens frame that holds a lens so as to be movable forward and backward in an optical axis direction of an optical lens, and a transmitting member that transmits to the lens frame a driving force generated by a strain deformation of a shape memory alloy member that exhibits a predetermined hysteresis characteristic between a temperature and an amount of deformation. The lens drive control apparatus includes a control section that, at a timing at which an instruction that causes the lens frame to move forward or backward stops, performs control that changes a temperature of the shape memory alloy member to a temperature belonging to a dead zone of the predetermined hysteresis characteristic.

5 Claims, 17 Drawing Sheets

LENS DRIVE CONTROL APPARATUS, LENS DRIVE APPARATUS AND ENDOSCOPE SYSTEM

CROSS REFERENCE TO RELATED APPLICATION

This application is a continuation application of PCT/JP2010/054660 filed on Mar. 18, 2010 and claims benefit of Japanese Application No. 2009-090396 filed in Japan on Apr. 2, 2009, the entire contents of which are incorporated herein by this reference.

BACKGROUND OF THE INVENTION

1. Field of the Invention

The present invention relates to a lens drive control apparatus, a lens drive apparatus, and an endoscope system, and more particularly to a lens drive control apparatus, a lens drive apparatus, and an endoscope system in which a lens can be moved along an optical axis direction.

2. Description of the Related Art

Endoscopes are conventionally widely used in the medical field and industrial field or the like. In some endoscopes, an image pickup apparatus is used that can realize tele photographing and wide photographing by moving an observation optical system in an optical axis direction.

More specifically, for example, Japanese Patent Application Laid-Open Publication No. 2008-194178 discloses an image pickup apparatus that is equipped with a moving lens frame to which a moving lens is mounted, and to which an actuator is mounted that causes the moving lens frame to move forward or backward according to a supply state of an electric current to a wire formed by a shape memory alloy (hereunder, referred to as "SMA"). Japanese Patent Application Laid-Open Publication No. 2008-194178 also discloses a configuration example in a case where the aforementioned image pickup apparatus is applied to a distal end portion of an endoscope.

SUMMARY OF THE INVENTION

A lens drive control apparatus according to one aspect of the present invention controls a lens drive system that has a lens frame that holds a lens so as to be movable forward and backward in an optical axis direction of an optical lens, and a transmitting member that transmits to the lens frame a driving force generated by a strain deformation of a shape memory alloy member that exhibits a predetermined hysteresis characteristic between a temperature and an amount of deformation; the lens drive control apparatus including a control section that, at a timing at which an instruction that causes the lens frame to move forward or backward stops, performs control that changes a temperature of the shape memory alloy member to a temperature belonging to a dead zone of the predetermined hysteresis characteristic.

A lens drive apparatus according to another aspect of the present invention has: a lens frame that holds a lens so as to be movable forward and backward in an optical axis direction of an optical lens; a shape memory alloy member; and a transmitting member that is provided with a clearance along the optical axis direction with respect to the lens frame, and that transmits a driving force generated by a strain deformation of the shape memory alloy member to the lens frame.

A lens drive apparatus according to a further aspect of the present invention has: a lens frame that holds a lens so as to be movable forward and backward in an optical axis direction of an optical lens; a transmitting member that is provided with a clearance along the optical axis direction with respect to the lens frame, and that transmits to the lens frame a driving force generated by a strain deformation of a shape memory alloy member that exhibits a predetermined hysteresis characteristic between a temperature and an amount of deformation; and a control section that, at a timing at which an instruction that causes the lens frame to move forward or backward stops, performs control that moves the transmitting member to a position that is separated from the lens frame along the optical axis direction, and changes a temperature of the shape memory alloy member to a temperature belonging to a dead zone of the predetermined hysteresis characteristic.

An endoscope system according to a further aspect of the present invention includes: an endoscope in which a lens frame that holds a lens so as to be movable forward and backward in an optical axis direction of an optical lens, and a transmitting member that is provided with a clearance along the optical axis direction with respect to the lens frame and that transmits to the lens frame a driving force generated by a strain deformation of a shape memory alloy member that exhibits a predetermined hysteresis characteristic between a temperature and an amount of deformation are provided in a distal end portion; and a control section that, at a timing at which an instruction that causes the lens frame to move forward or backward stops, performs control that moves the transmitting member to a position that is separated from the lens frame along the optical axis direction, and changes a temperature of the shape memory alloy member to a temperature belonging to a dead zone of the predetermined hysteresis characteristic.

DETAILED DESCRIPTION OF THE PREFERRED EMBODIMENT(S)

Hereunder, embodiments of the present invention are described with reference to the drawings.

(First Embodiment)

FIGS. 1 to 11 relate to the first embodiment of the present invention.

Figure 1:
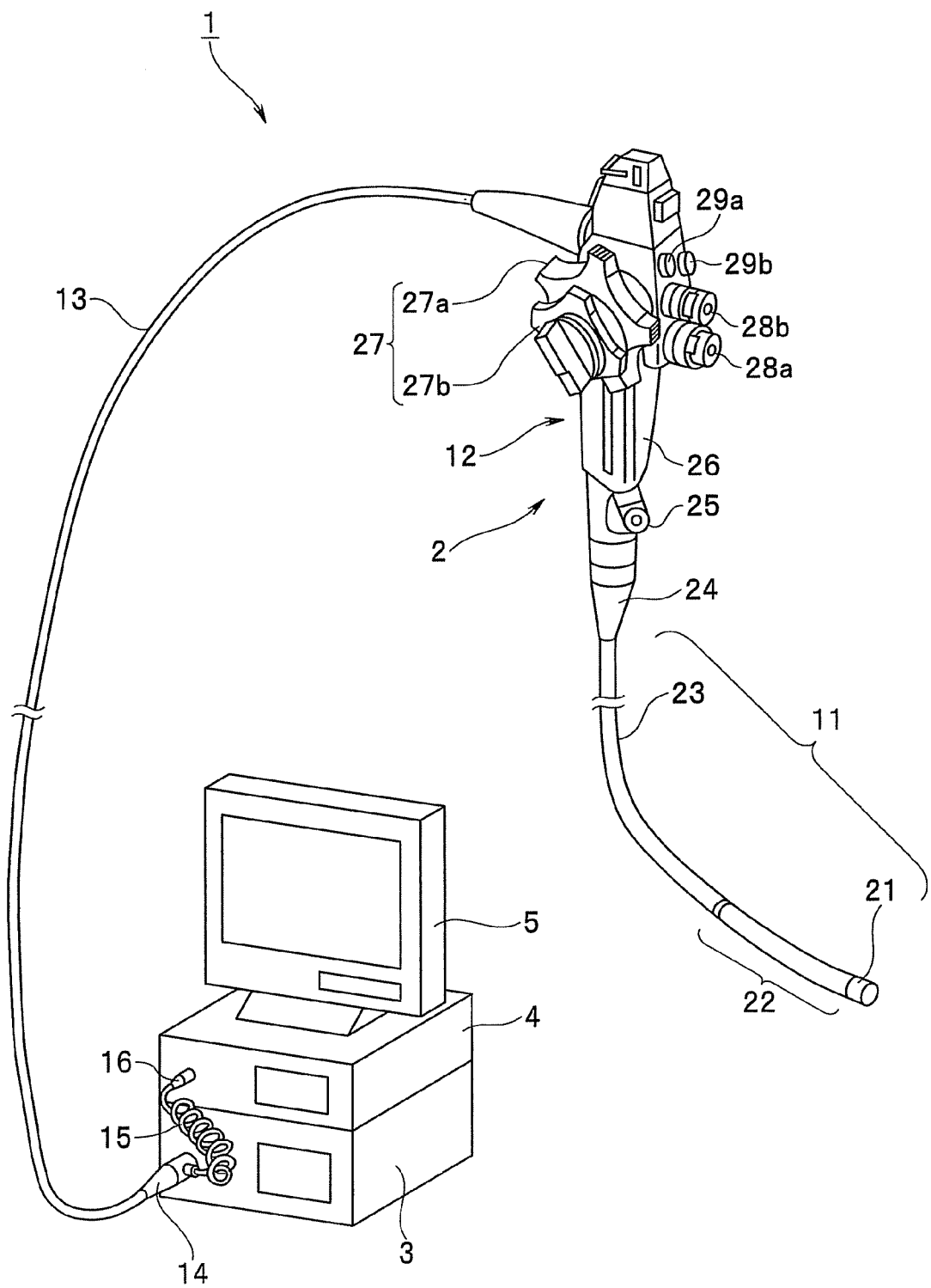
FIG. 1 is a view that illustrates a configuration of principal parts of an endoscope system according to an embodiment of the present invention.

As shown in FIG. 1, an endoscope system 1 according to an embodiment of the present invention includes an endoscope 2 that picks up an image of an object inside a living body and outputs an image pickup signal, a light source apparatus 3 that supplies an illuminating light for illuminating the object, a processor 4 that converts the image pickup signal into a video signal and outputs the video signal, and a monitor 5 that displays an image of the object in accordance with the video signal.

The endoscope 2 includes an insertion portion 11 that has a shape and dimensions that can be inserted into a living body, an operation portion 12, and a universal cable 13 having one end side extending from a side face of the operation portion 12. The endoscope 2 also includes a scope connector 14 that connects the other end side of the universal cable 13 and the light source apparatus 3, a coiled scope cable 15 having one end side extending from the scope connector 14, and an electrical connector portion 16 that connects the other end side of the scope cable 15 and the processor 4.

The insertion portion 11 includes a distal end portion 21, a bending portion 22, and a flexible tube portion 23 that are provided in a connected arrangement in order from the distal end thereof. An unshown light guide bundle for transmitting an illuminating light that is emitted from the light source apparatus 3 is insertedly disposed inside each portion from the distal end portion 21 to the scope connector 14.

A distal end opening, an observation window, a plurality of illuminating windows, an observation window cleaning opening, and an observation object cleaning opening, all of which are unshown in the drawings, are provided at a distal end face of the distal end portion 21.

An image pickup unit that is described later is disposed on the inside of the distal end portion 21 at a rear side of the aforementioned observation window. Further, a light exit end of the unshown light guide bundle is disposed on the inside of the distal end portion 21 at a rear side of the aforementioned plurality of illuminating windows.

An unshown observation window cleaning nozzle is provided at the distal end portion 21. The observation window cleaning nozzle constitutes an opening of an unshown cleaning tube that is inserted through the inside of each portion from the distal end portion 21 to the universal cable 13. The cleaning tube is connected to an unshown cleaning tank and compressor at an end on the light source apparatus 3 side of the universal cable 13.

The operation portion 12 includes a bend preventing portion 24 from which the insertion portion 11 extends, a forceps opening 25 that is arranged at a side portion on a lower portion side, an operation portion main body 26 that has a configuration that can be grasped by an operator, a bending operation portion 27 that includes two bending operation knobs 27a and 27b provided on an upper portion side, an air/water supply switch 28a which can be operated to issue an instruction to perform an air/water supply operation, a suction switch 28b which can be operated to issue an instruction to perform a suction operation, a tele switch 29a which can be operated to issue an instruction to perform an operation relating to tele photographing, and a wide switch 29b which can be operated to issue an instruction to perform an operation relating to wide photographing. Further, an unshown treatment instrument channel is insertedly disposed inside each portion from the forceps opening 25 of the operation portion 12 to the distal end opening of the distal end portion 21.

Next, the configuration of the image pickup unit inside the distal end portion 21 is described.

An image pickup unit 30 is insertedly arranged in an unshown distal end rigid member provided inside the distal end portion 21. The image pickup unit 30 has a configuration that can realize zooming functions that include tele photographing and wide photographing by means of a moving lens (and moving lens frame), described later, moving forward and backward along an optical axis direction.

Figure 2:
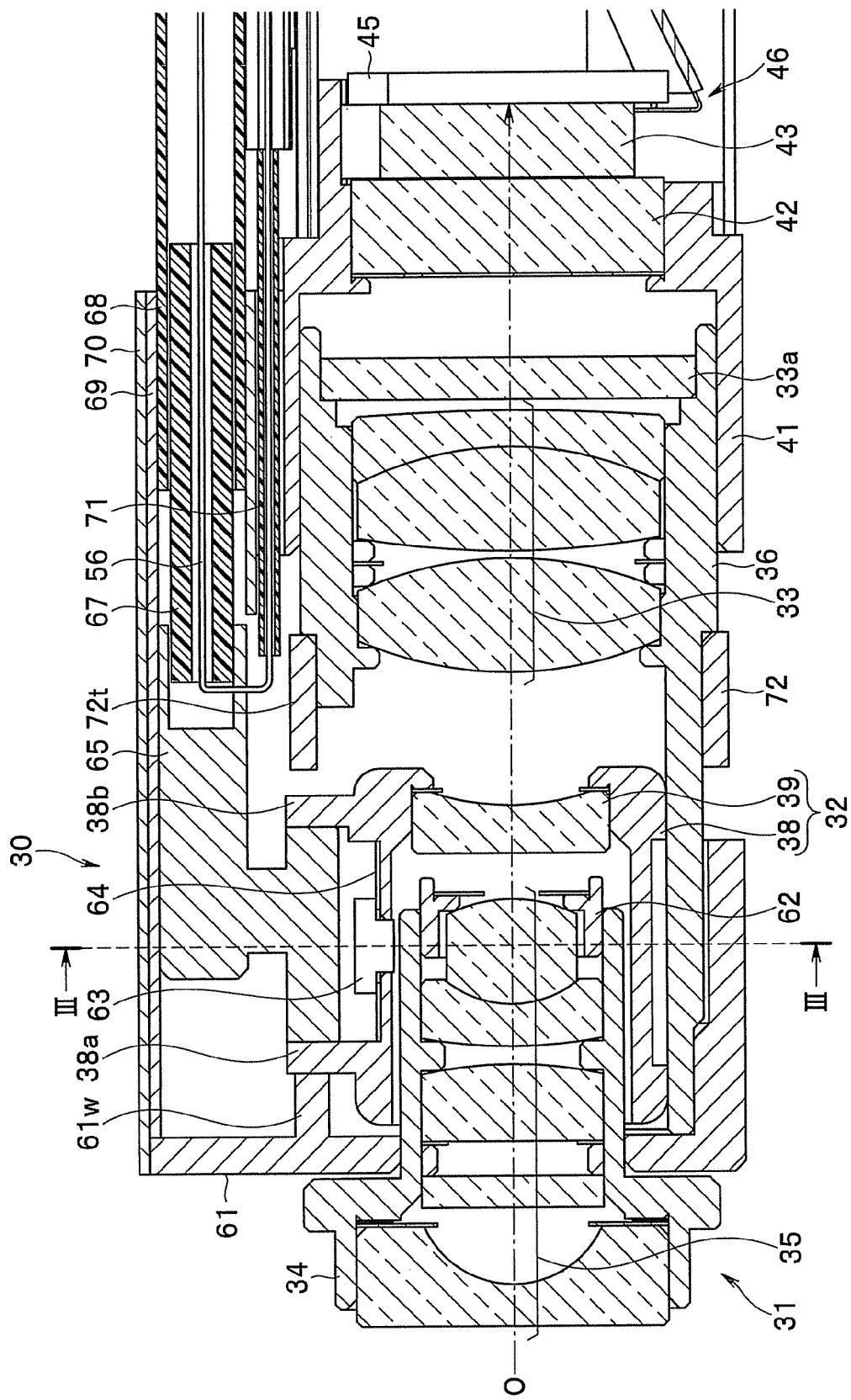
FIG. 2 is a sectional view that illustrates an example of an internal configuration of an image pickup unit according to a first embodiment.

As shown in FIG. 2, the image pickup unit 30 includes, in order from the distal end side thereof, a front group lens frame 34 as a fixed lens frame that holds front group lenses 35 that include a plurality of objective lenses and which is included in a front group lens unit 31; a rear group lens frame 36 as a fixed lens frame that holds rear group lenses 33 that include a plurality of objective lenses, and an optical member 33a; a moving lens frame 38 that is provided between the front group lenses 35 and the rear group lenses 33 and which constitutes an outer shape of a moving lens unit 32 as a mobile body that holds a moving lens 39; and an image sensor unit 46 that is provided to the rear of the optical member 33a.

Each portion of the image sensor unit 46 is held by an image sensor holding frame 41. The image sensor unit 46 includes within the image sensor holding frame 41, in order from the distal end thereof, two optical members 42 and 43, an image sensor chip 45 that converts an optical image of an object into an image pickup signal and outputs the image pickup signal, and an unshown multilayer substrate. The image sensor chip 45 and the multilayer substrate are electrically connected by a flexible printed circuit (FPC). Further, the multilayer substrate is connected with an unshown cable in which a plurality of signal wires including a wire that transmits an image pickup signal that is outputted from the image sensor chip 45 are bundled. The unshown cable is insertedly disposed inside the endoscope 2, and is electrically connected to the processor 4 via the universal cable 13, the scope cable 15, and the electrical connector portion 16.

A rear end portion of the front group lens frame 34 is fittingly joined with the front end portion of the rear group lens frame 36 and a lens frame pressing member 61. Further, a lens holding frame 62 for holding an objective lens that is disposed at a rearmost end of the front group lenses 35 is fitted to the rear end portion of the front group lens frame 34.

Meanwhile, a rear end portion of the rear group lens frame 36 is insertedly fixed in a front end portion of the image sensor holding frame 41. Further, an adjustment ring 72 for performing adjustment and fixing of a focal position of the rear group lenses 33 is provided in the rear group lens frame 36.

The moving lens unit 32 is disposed on a rear side of the front group lens unit 31 at a place that corresponds to an inner side of the rear group lens frame 36, and is configured to be slidable along the direction of an optical axis O.

In this connection, according to the present embodiment, a movable limit position on a wide side (front side) of the moving lens unit 32 is determined by a regulating portion 61w provided on an upper side of the lens frame pressing member 61. In other words, the moving lens unit 32 can slide to the wide side until a front face portion of an extending portion 38a that is formed in an extending manner to an upper side from a front portion of the moving lens frame 38 contacts against a rear face portion of the regulating portion 61w.

Further, according to the present embodiment, a movable limit position on a tele side (rear side) of the moving lens unit 32 is determined by a regulating portion 72t on an upper side of the adjustment ring 72. In other words, the moving lens unit 32 can slide to the tele side until a rear face portion of an extending portion 38b that is formed in an extending manner to an upper side from a rear portion of the moving lens frame 38 contacts against a front face portion of the regulating portion 72t.

Meanwhile, a leaf spring 64 whose upper portion is fixed by a screw 63 is provided in the moving lens frame 38 of the moving lens unit 32.

Figure 3:
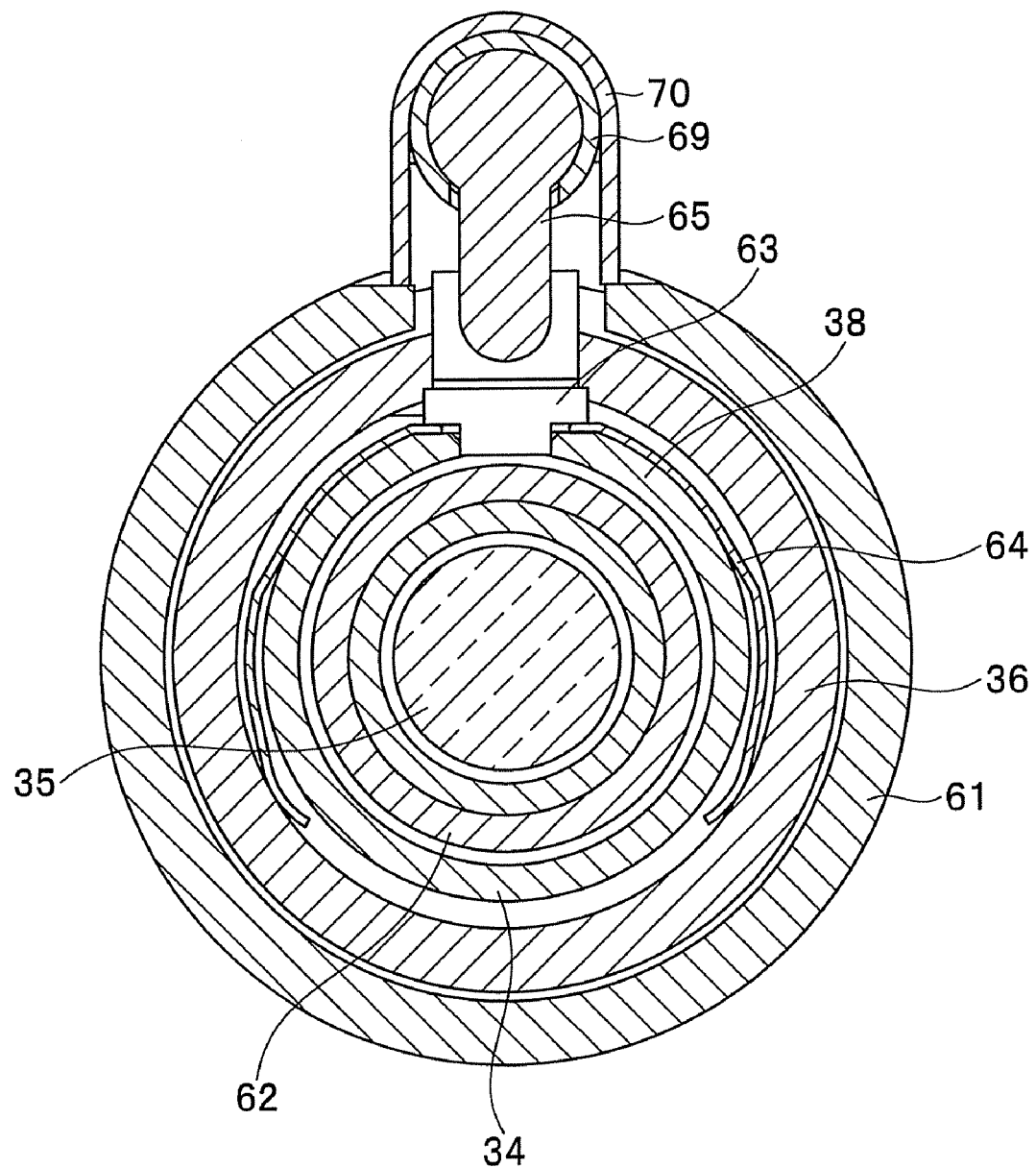
FIG. 3 is a sectional view along a line III-III in FIG. 2.

As shown in FIG. 3, the leaf spring 64 is configured so that, by being urged in the outer circumferential direction of the moving lens frame 38, at least one part of the leaf spring 64 contacts against an inner circumferential face of the rear group lens frame 36 so that the leaf spring 64 can generate a resistance force of a degree that ensures the moving lens unit 32 does not move under its own weight (according to the present embodiment, a frictional force of a degree that can hold the moving lens unit 32), with respect to the inner circumferential face of the rear group lens frame 36.

A connecting portion 65 that transmits a driving force for sliding the moving lens frame 38 along the optical axis O direction is provided on an upper portion of the moving lens frame 38.

A lower portion of the connecting portion 65 is integrally joined to the extending portions 38a and 38b of the moving lens frame 38. According to the present embodiment, a clearance in the optical axis O direction between the extending portions 38a and 38b is eliminated by adopting this configuration.

A front end portion of a tube member 67 that is formed by an insulating member is adhesively fixed in an opening formed in a rear end of an upper portion of the connecting portion 65. A portion from a mid-way portion of the tube member 67 to a rear end portion thereof is insertedly fixed in a front end portion of a guide pipe 68 that is formed by an insulating member.

Figure 4:
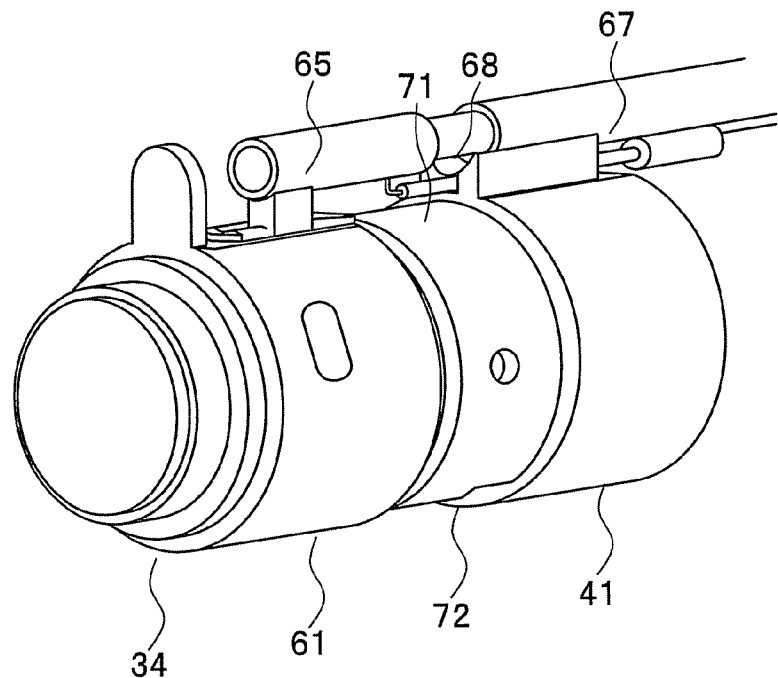
FIG. 4 is a perspective view that illustrates an example of an external configuration of the image pickup unit according to the first embodiment.
Figure 5:
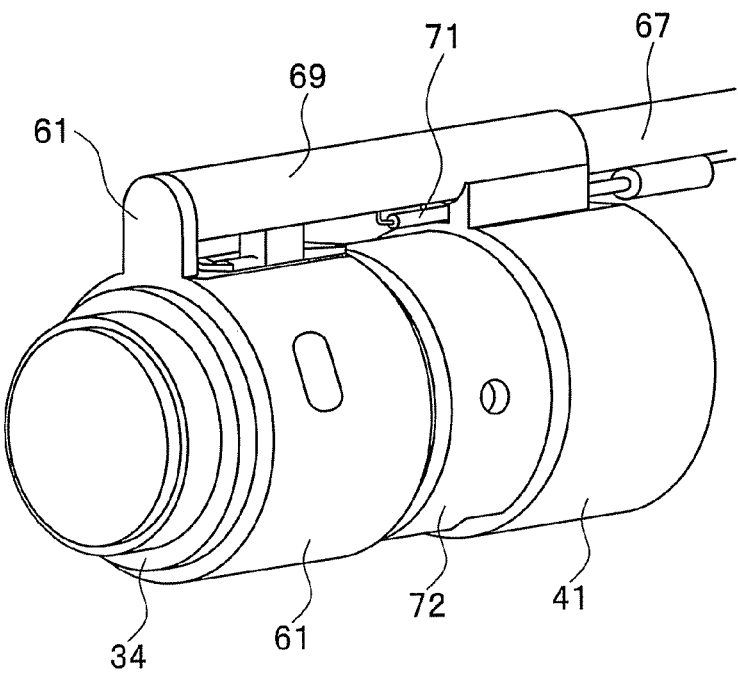
FIG. 5 is a perspective view that illustrates an example of a case where a guide member is mounted to the image pickup unit shown in FIG. 4.
Figure 6:
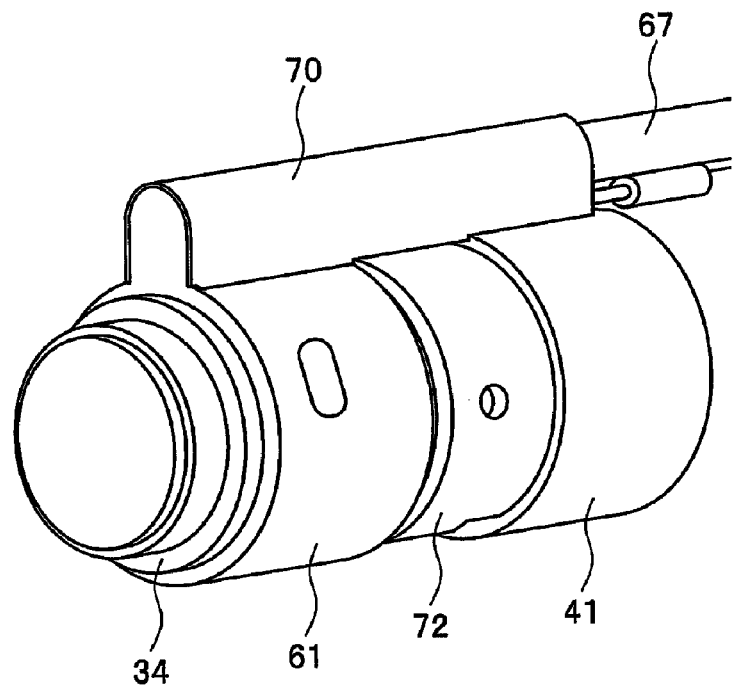
FIG. 6 is a perspective view that illustrates an example of a case where a cover member is mounted to the image pickup unit shown in FIG. 5.

Meanwhile, as shown in FIG. 3, FIG. 4, and FIG. 5, the upper portion of the connecting portion 65, the tube member 67, and the front end portion of the guide pipe 68 are disposed inside a guide member 69. Further, as shown in FIG. 3, FIG. 5, and FIG. 6, the guide member 69 and a tube member 71 are covered by a cover member 70.

An SMA wire 56 is formed so as to relax under an ordinary temperature environment, and to exhibit a predetermined hysteresis characteristic between a temperature and an amount of deformation. Further, as a predetermined relaxed state thereof, the SMA wire 56 is inserted through the inside of the tube member 67 and the guide pipe 68, is folded back inside an opening formed in the rear end of the upper portion of the connecting portion 65, and is inserted through the inside of the tube member 71. Furthermore, as shown in FIG. 2, a part of the folded back portion of the SMA wire 56 is directly joined to the connecting portion 65.

According to the above described configuration, the connecting portion 65 as a transmitting member can transmit to the moving lens frame 38 a driving force that is produced by a strain deformation of an SMA wire that is described later. That is, the lens drive system according to the present embodiment includes the moving lens frame 38 and the connecting portion 65.

Figure 7:
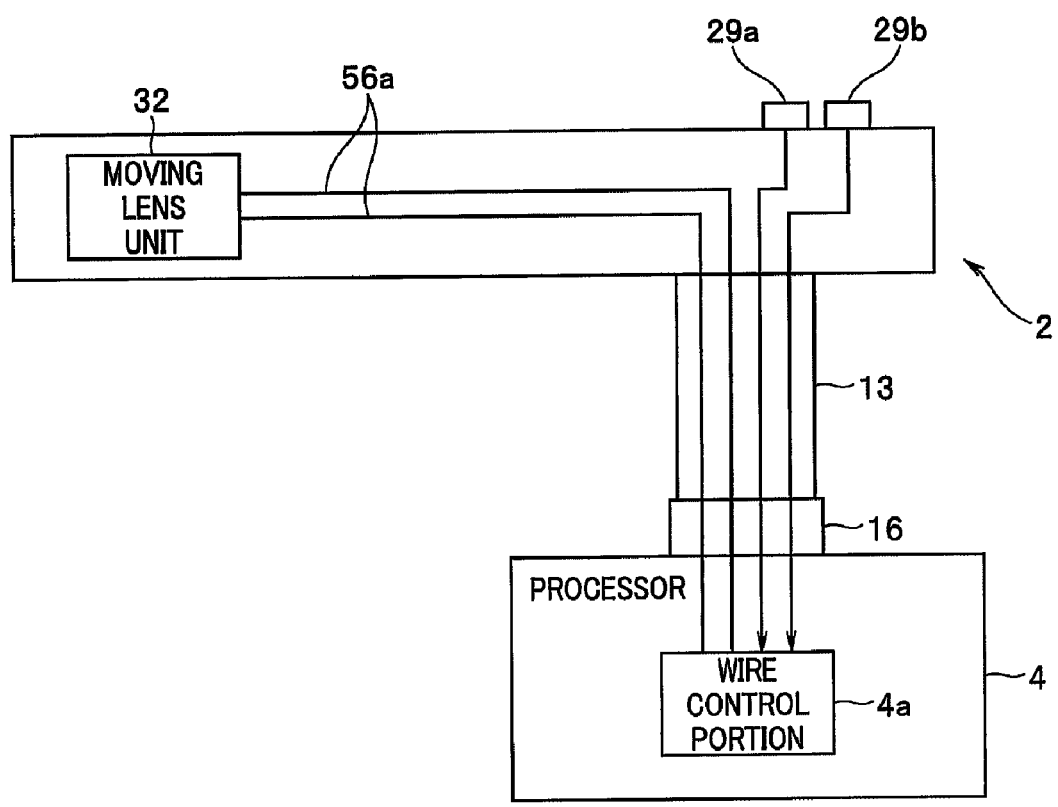
FIG. 7 is a view that shows an outline of an electrical connection relationship among portions including a lens drive system.

In this connection, for example, as shown in FIG. 7, opposite end portions of the SMA wire 56 are respectively connected to electrically conductive cables 56a. Further, the two cables 56a are insertedly disposed inside the endoscope 2, the universal cable 13 and the electrical connector portion 16, and are respectively connected to a wire control portion 4a of the processor 4 that has a function as a lens drive control apparatus.

Meanwhile, the tele switch 29a and the wide switch 29b are respectively connected to the wire control portion 4a of the processor 4 via signal wires that are insertedly disposed inside the endoscope 2, the universal cable 13 and the electrical connector portion 16.

The wire control portion 4a applies a voltage in accordance with an instruction made at the tele switch 29a or the wide switch 29b to the electrically conductive cables 56a.

When the wire control portion 4a detects that an instruction has been made at the tele switch 29a, the wire control portion 4a performs control for increasing the applied voltage to the cables 56a to a level that is greater than the currently applied voltage. An increase in the voltage applied to the cables 56a acts to increase the temperature of the SMA wire 56 and also decrease the amount of deformation of the SMA wire 56. As a result, a driving force that accompanies a contraction in the length of the SMA wire 56 from its current state arises at the connecting portion 65, and the moving lens frame 38 is slid to the tele side (rear side) by the driving force.

Meanwhile, when the wire control portion 4a detects that an instruction has been made at the wide switch 29b, the wire control portion 4a performs control for decreasing an applied voltage to the cables 56a to a level that is less than the currently applied voltage. The decrease in the voltage applied to the cables 56a acts to lower the temperature of the SMA wire 56 and increase the amount of deformation of the SMA wire 56. As a result, a driving force that accompanies an increase in the length of the SMA wire 56 from its current state arises at the connecting portion 65, and the moving lens frame 38 is slid to the wide side (front side) by the driving force.

In this connection, the wire control portion 4a is not limited to a component that is provided inside the processor 4, and, for example, may be a component that is provided inside the operation portion 12 of the endoscope 2.

Figure 8:
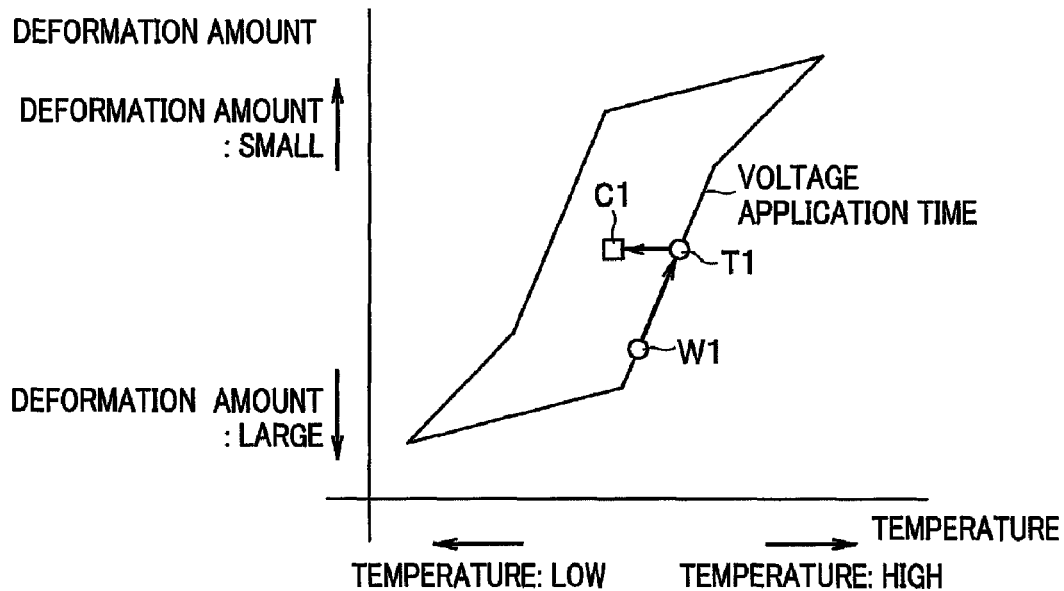
FIG. 8 is a view that illustrates a manner in which a state of an SMA changes when control of the first embodiment is performed in accordance with a tele-photographing instruction.
Figure 10:
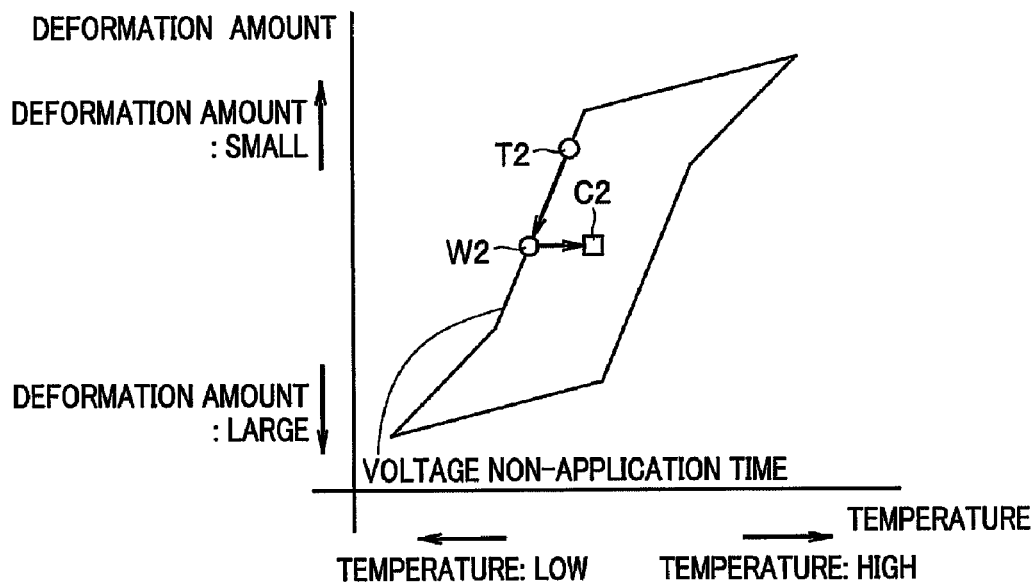
FIG. 10 is a view that illustrates a manner in which a state of an SMA changes when control of the first embodiment is performed in accordance with a wide-photographing instruction.

Control performed by the wire control portion 4a as an action of the present embodiment will now be described in detail. In this connection, it is assumed that the SMA wire 56 has, for example, a hysteresis characteristic as shown in FIG. 8 and FIG. 10 between a temperature and an amount of deformation. Further, it is assumed that the hysteresis characteristics shown in FIG. 8 and FIG. 10 are the same as each other.

Figure 9:
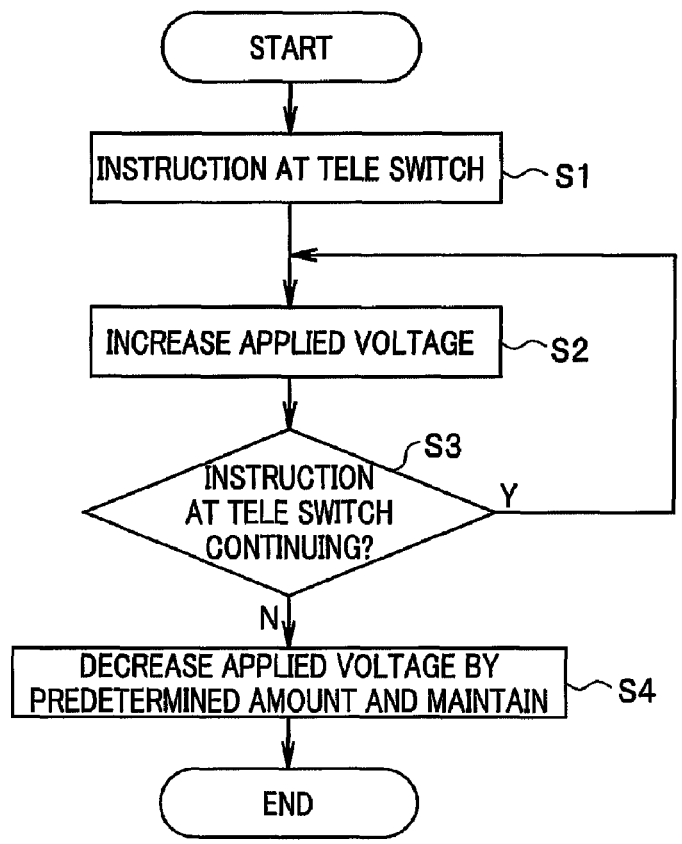
FIG. 9 is a flowchart that illustrates an example of control that is performed in accordance with a tele-photographing instruction in the first embodiment.

The wire control portion 4a, for example, detects that the SMA wire 56 exhibits a state represented by a reference symbol W1 in FIG. 8 by measuring a resistance value of the SMA wire 56 at a timing at which an instruction is made at the tele switch 29a (step S1 in FIG. 9). Based on the detection result, the wire control portion 4a performs control for increasing the applied voltage to the cables 56a (step S2 in FIG. 9), to thereby increase the temperature of the SMA wire 56. Further, the wire control portion 4a continues the control for increasing the applied voltage to the cables 56a while the instruction is continuing at the tele switch 29a (step S3 in FIG. 9).

When the applied voltage to the cables 56a continues to be increased, the temperature of the SMA wire 56 increases along a line for a time of voltage application in the hysteresis characteristic shown in FIG. 8. As a result, the amount of deformation of the SMA wire 56 gradually decreases and the SMA wire 56 tenses and contracts. Hence, a driving force towards the rear side of the distal end portion 21 is generated at the connecting portion 65. The moving lens frame 38 is slid to the tele side by the driving force generated at the connecting portion 65.

Thereafter, upon detecting that the instruction at the tele switch 29a has stopped (step S3 in FIG. 9), the wire control portion 4a performs control to decrease the applied voltage to the cables 56a by a predetermined amount (for example, approximately 20%) from the applied voltage at the time the instruction stopped, and to maintain the applied voltage at the decreased amount (step S4 in FIG. 9).

More specifically, for example, when the aforementioned control is performed at a timing at which the SMA wire 56 is in a state indicated by a reference symbol T1 in FIG. 8, the temperature of the SMA wire 56 decreases in accordance with the amount of decrease in the applied voltage to the cables 56a. Accompanying this temperature decrease, the state of the SMA wire 56 changes from the state T1 positioned on a line for a time of a voltage application in the hysteresis characteristic shown in FIG. 8 to a state C1 positioned in a dead zone of the hysteresis characteristic shown in FIG. 8.

That is, according to the above described control, the applied voltage to the cables 56a is maintained at a level that is in a dead zone of the hysteresis characteristic shown in FIG. 8. Further, the moving lens unit 32 is held in the position thereof after the aforementioned control has been performed, by an urging force of the leaf spring 64. Therefore, for example, after an instruction at the tele switch 29a stops, even if a disturbance arises in response to a change in an ambient temperature around the distal end portion 21, the position of the moving lens frame 38 does not fluctuate because the state of the SMA wire 56 does not change.

Figure 11:
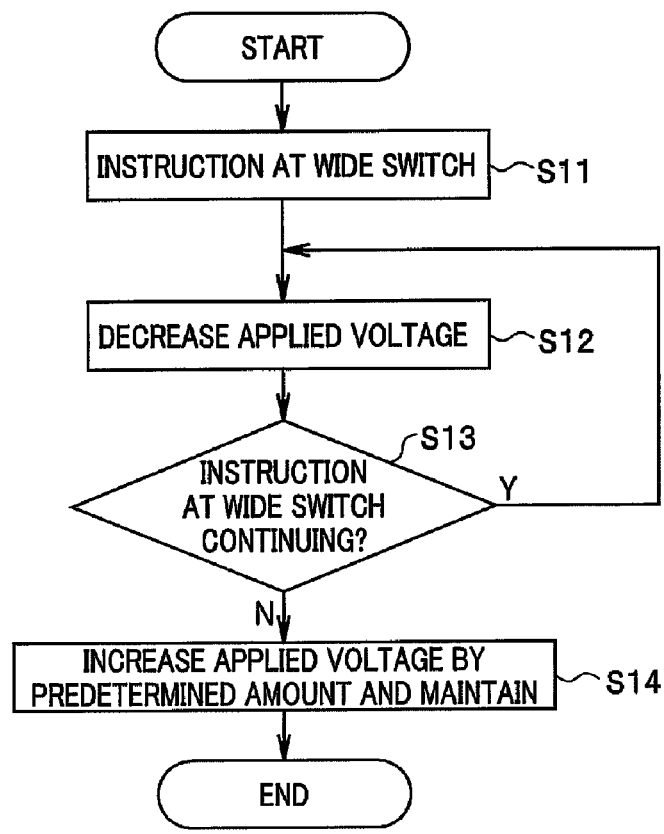
FIG. 11 is a flowchart that illustrates an example of control that is performed in accordance with a wide-photographing instruction according to the first embodiment.

Meanwhile, the wire control portion 4a detects, for example, that the SMA wire 56 exhibits a state represented by a reference symbol T2 in FIG. 10 by measuring a resistance value of the SMA wire 56 at a timing at which an instruction is made at the wide switch 29b (step S11 in FIG. 11). The wire control portion 4a reduces the temperature of the SMA wire 56 by performing control to decrease the applied voltage to the cables 56a based on the detection result (step S12 in FIG. 11). Further, the wire control portion 4a continues the control to decrease the applied voltage to the cables 56a while the instruction is continuing at the wide switch 29b (step S13 in FIG. 11).

When the applied voltage to the cables 56a continues to be decreased, the temperature of the SMA wire 56 decreases along a line for a time of non-application of a voltage in the hysteresis characteristic shown in FIG. 10. As a result, the amount of deformation of the SMA wire 56 gradually increases, and the SMA wire 56 relaxes and lengthens. Hence, a driving force towards the front side of the distal end portion 21 is generated at the connecting portion 65. Thus, the moving lens frame 38 is slid to the wide side by the driving force that is generated at the connecting portion 65.

Thereafter, upon detecting that the instruction at the wide switch 29b has stopped (step S13 in FIG. 11), the wire control portion 4a performs control to increase the applied voltage to the cables 56a by a predetermined amount (for example, approximately 20%) from the applied voltage at the time that the instruction stopped, and to maintain the applied voltage at that increased amount (step S14 in FIG. 11).

More specifically, for example, when the aforementioned control is performed at a timing at which the SMA wire 56 exhibits a state indicated by a reference symbol W2 in FIG. 10, the temperature of the SMA wire 56 increases in accordance with the amount of increase in the applied voltage to the cables 56a. Accompanying this increase in temperature, the state of the SMA wire 56 changes from the state W2 positioned on the line for a time of non-application of a voltage in the hysteresis characteristic shown in FIG. 10 to a state C2 positioned in a dead zone of the hysteresis characteristic shown in FIG. 10.

That is, according to the above described control, the applied voltage to the cables 56a is maintained in a dead zone of the hysteresis characteristic shown in FIG. 10. Further, the moving lens unit 32 is held in the position thereof after the aforementioned control has been performed, by an urging force of the leaf spring 64. Therefore, for example, after an instruction at the wide switch 29b stops, even if a disturbance arises in response to a change in the ambient temperature around the distal end portion 21, the position of the moving lens frame 38 does not fluctuate because the state of the SMA wire 56 does not change.

According to the configuration and actions of the present embodiment as described above, even when a change in the ambient temperature around the distal end portion 21 of the endoscope 2 acts as a disturbance, the state of the SMA wire 56 does not change and the moving lens frame 38 does not move. It is thus possible to prevent movement of the moving lens 39 to a position to which movement thereof is originally not intended.

(Second Embodiment)

FIGS. 12 to 22 relate to a second embodiment of the present invention.

In the following description, a detailed description of portions that have similar components to those of the first embodiment is omitted. The configuration of the present embodiment is substantially the same as that of the endoscope system 1 according to the first embodiment. Therefore, the description according to the present embodiment mainly relates to portions that are different from the endoscope system 1 of the first embodiment.

Figure 12:
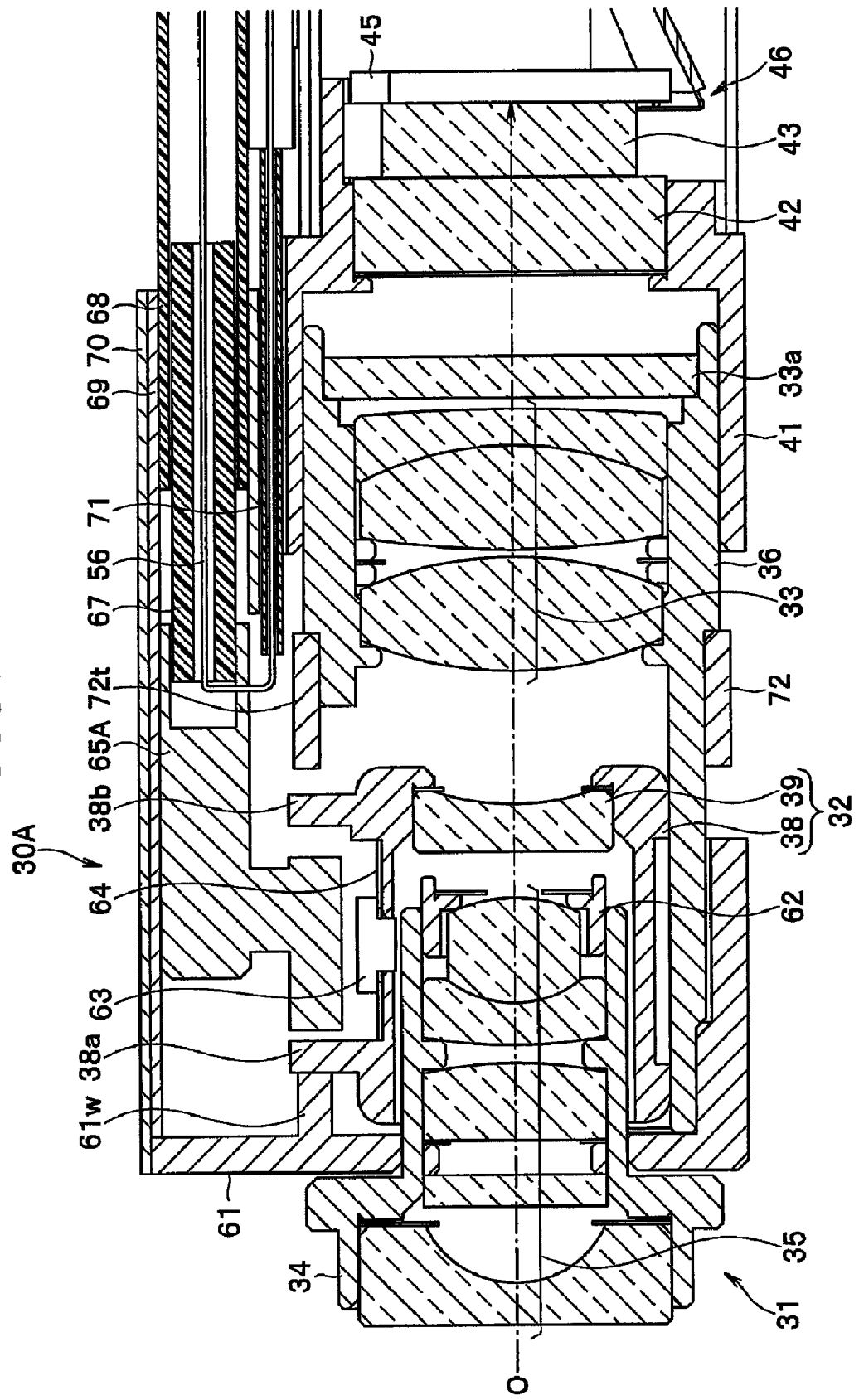
FIG. 12 is a sectional view that illustrates an example of an internal configuration of an image pickup unit according to a second embodiment.

As shown in FIG. 12, an image pickup unit 30A of the present embodiment includes a moving element 65A as a transmitting member instead of the connecting portion 65 that is provided in the image pickup unit 30. The other portions of the image pickup unit 30A are approximately the same as in the image pickup unit 30, and hence a detailed description of such portions is omitted.

Figure 13:
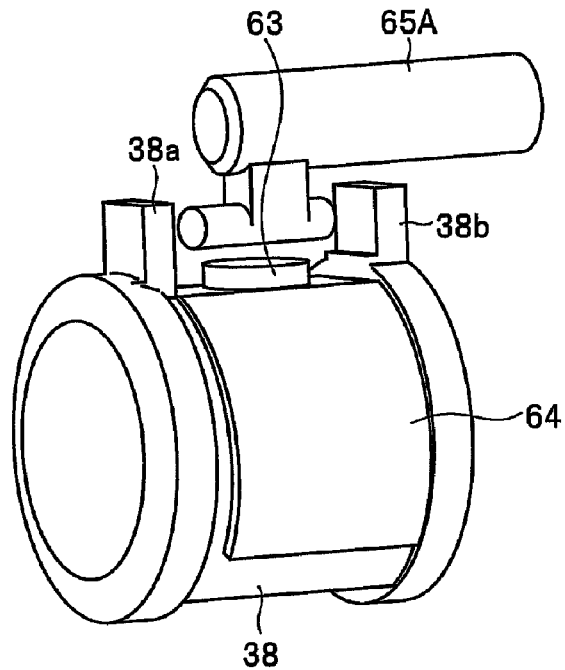
FIG. 13 is a perspective view that illustrates an example of a configuration of a moving element and a moving lens frame according to the second embodiment.

As shown in FIG. 12 and FIG. 13, a lower portion of the moving element 65A is disposed so as to have a clearance with respect to a rear face side of the extending portion 38a and a front face side of the extending portion 38b. In other words, a clearance is provided along the optical axis O direction between the extending portions 38a and 38b of the moving lens frame 38 and the lower portion of the moving element 65A. The upper portion of the moving element 65A has a configuration that is similar to that of the connecting portion 65 described in the first embodiment.

Figure 14:
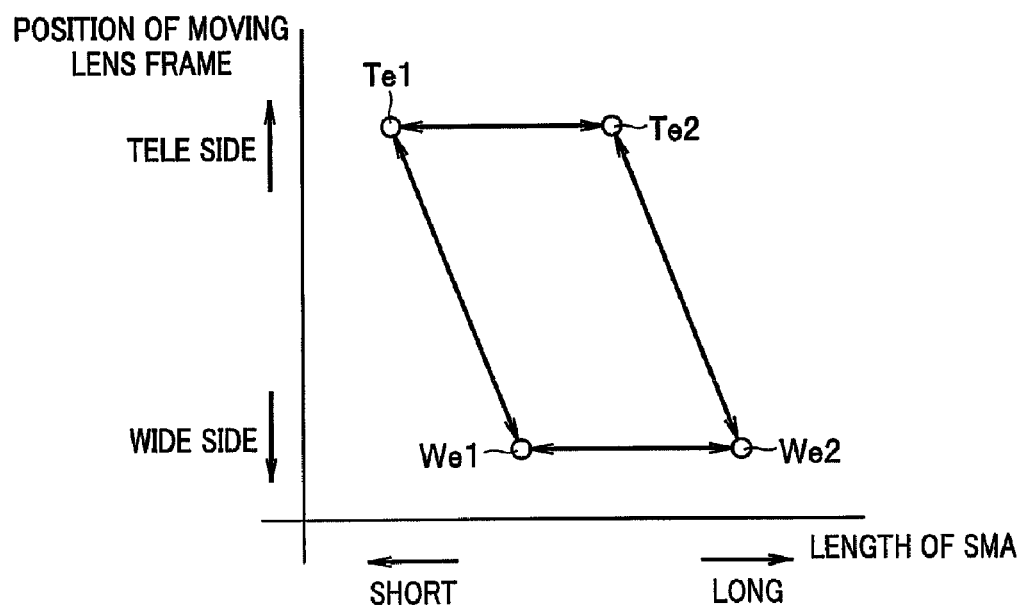
FIG. 14 is a view that illustrates an example of mechanical hysteresis that is generated by the configuration of the moving element and the moving lens frame according to the second embodiment.
Figure 15:
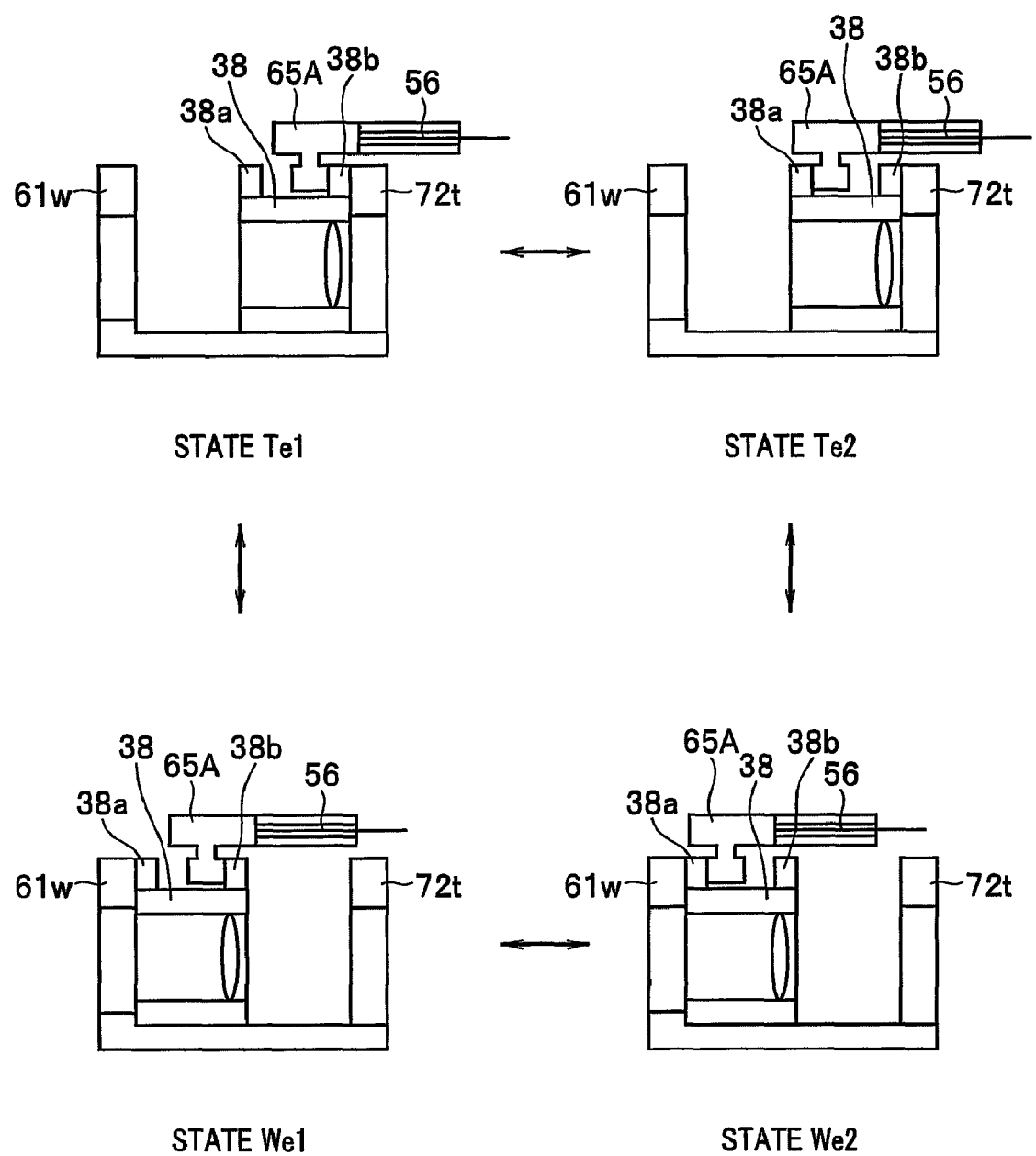
FIG. 15 is a view that illustrates a representative example of positions that the moving element can take when the moving lens frame reaches a movable limit position.

According to the above described configuration, a relationship between the length of the SMA wire 56 and a position of the moving lens frame 38 exhibits a mechanical hysteresis as shown, for example, in FIG. 14 and FIG. 15.

A state Te1 shown in FIG. 14 and FIG. 15 is a state in which a rear face portion of the extending portion 38b and a front face portion of the regulating portion 72t are in contact, and a front face portion of the extending portion 38b and a rear face portion of the lower portion of the moving element 65A in contact. In such a state, by the SMA wire 56 relaxing and lengthening, the moving element 65A is moved to the wide side (front side) while the rear face portion of the extending portion 38b and the front face portion of the regulating portion 72t remain in contact. Thereafter, by the moving element 65A moving to the wide side (front side), the length of the SMA wire 56 and the position of the moving lens frame 38 change from the state Te1 to a state Te2.

The state Te2 shown in FIG. 14 and FIG. 15 is a state in which the rear face portion of the extending portion 38b and the front face portion of the regulating portion 72t are in contact, and the rear face portion of the extending portion 38a and the front face portion of the moving element 65A are in contact. In this state, by the SMA wire 56 relaxing and lengthening, the moving lens frame 38 is moved to the wide side (front side) while the rear face portion of the extending portion 38a and the front face portion of the moving element 65A remain in contact. Thereafter, by the moving lens frame 38 moving to the wide side (front side), the length of the SMA wire 56 and the position of the moving lens frame 38 change from the state Te2 to a state We2.

The state We2 shown in FIG. 14 and FIG. 15 is a state in which the front face portion of the extending portion 38a and the rear face portion of the regulating portion 61w are in contact, and the rear face portion of the extending portion 38a and the front face portion of the moving element 65A are in contact. In this state, by the SMA wire 56 tensing and contracting, the moving element 65A is moved to the tele side (rear side) while the front face portion of the extending portion 38a and the rear face portion of the regulating portion 61w remain in contact. Thereafter, by the moving element 65A moving to the tele side (rear side), the length of the SMA wire 56 and the position of the moving lens frame 38 change from the state We2 to a state We1.

The state We1 shown in FIG. 14 and FIG. 15 is a state in which the front face portion of the extending portion 38a and the rear face portion of the regulating portion 61w are in contact, and the front face portion of the extending portion 38b and the rear face portion of the moving element 65A are in contact. In this state, by the SMA wire 56 tensing and contracting, the moving lens frame 38 is moved to the tele side (rear side) while the front face portion of the extending portion 38b and the rear face portion of the moving element 65A remain in contact. Thereafter, by the moving lens frame 38 moving to the tele side (rear side), the length of the SMA wire 56 and the position of the moving lens frame 38 change from the state We1 to the state Te1.

In this connection, as shown in FIG. 14 and FIG. 15, the length of the SMA wire 56 and the position of the moving lens frame 38 can change in the order of state Te1→Te2→We2→We1→Te1→ . . . and can also change in the order of state Te1→We1→We2→Te2→Te1→ . . . .

Control that the wire control portion 4a performs as an action of the present embodiment will now be described in detail. However, to simplify the description, only a case in which the length of the SMA wire 56 and the position of the moving lens frame 38 change in the order of state Te1→Te2→We2→We1→Te1→ . . . is described hereunder.

Figure 16:
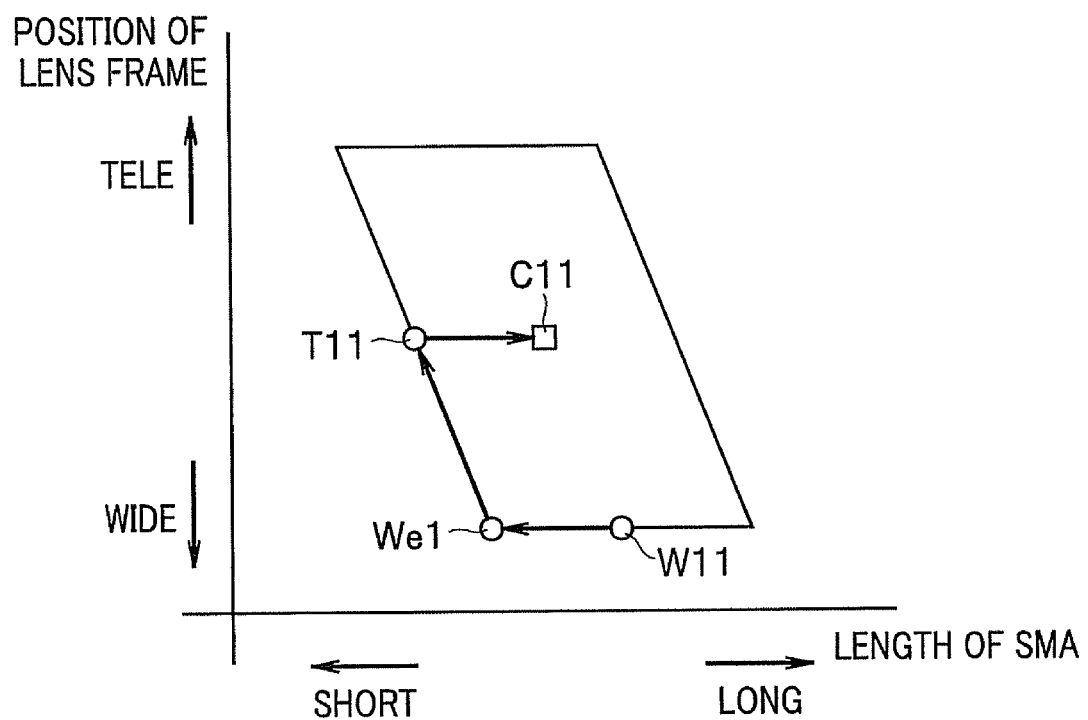
FIG. 16 is a view that illustrates a manner in which a length of an SMA wire and a position of the moving lens frame change when control of the second embodiment is performed in accordance with a tele-photographing instruction.
Figure 17:
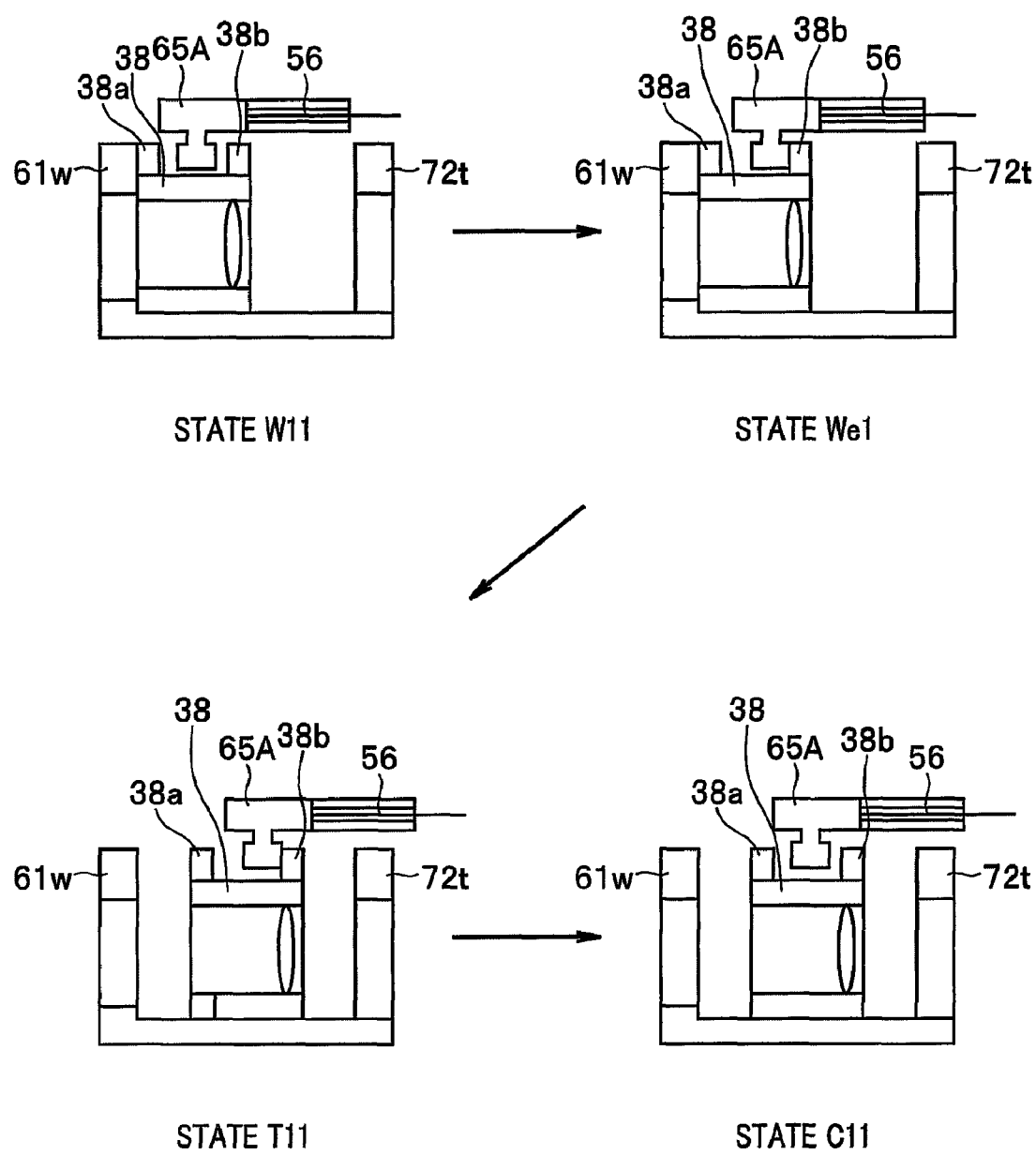
FIG. 17 is a view that illustrates a manner in which the moving element and the moving lens frame move in response to the control illustrated in FIG. 16.

When the moving lens frame 38 is, for example, at a furthest position on the wide side, the wire control portion 4a maintains an applied voltage to the cables 56a so as to enter a state W11 shown in FIG. 16 and FIG. 17.

The state W11 shown in FIG. 16 and FIG. 17 is a state in which the front face portion of the extending portion 38a and the rear face portion of the regulating portion 61w are in contact, and the moving element 65A is not in contact with either of the extending portions 38a and 38b. That is, in the state W11 shown in FIG. 16 and FIG. 17, the moving element 65A is disposed at a position that is separated from the moving lens frame 38 along the optical axis O direction.

Upon detecting that an instruction has been made at the tele switch 29a when in the state W11, the wire control portion 4a raises the temperature of the SMA wire 56 by performing control to increase the applied voltage to the cables 56a. The wire control portion 4a continues the control to increase the applied voltage to the cables 56a while the instruction at the tele switch 29a is continuing.

When the applied voltage to the cables 56a continues to be increased, the amount of deformation of the SMA wire 56 gradually decreases as a result of the temperature of the SMA wire 56 increasing, and the SMA wire 56 tenses and contracts. The contraction in the length of the SMA wire 56 causes the moving lens frame 38 that is in the state We1 to begin to slide to the tele side.

Thereafter, upon detecting that the instruction at the tele switch 29a has stopped, the wire control portion 4a performs control to decrease the applied voltage to the cables 56a by a predetermined amount from the applied voltage at the time that the instruction stopped, and to maintain the applied voltage at the decreased amount.

More specifically, for example, when the aforementioned control is performed in a state T11 shown in FIG. 16 and FIG. 17, the temperature of the SMA wire 56 falls in accordance with the amount of decrease in the applied voltage to the cables 56a. Accompanying this fall in temperature, the length of the SMA wire 56 and the position of the moving lens frame 38 change from the state T11 to a state C11 shown in FIG. 16 and FIG. 17.

The state C11 shown in FIG. 16 and FIG. 17 is a state in which the moving lens frame 38 is positioned approximately midway between the tele side and the wide side, the front face portion of the extending portion 38a and the rear face portion of the regulating portion 61w are not in contact, the rear face portion of the extending portion 38b and the front face portion of the regulating portion 72t are not in contact, and the moving element 65A is not in contact with either of the extending portions 38a and 38b. That is, in the state C11 shown in FIG. 16 and FIG. 17, the moving element 65A is disposed at a position that is separated from the moving lens frame 38 along the optical axis O direction.

More specifically, according to the above described control, an applied voltage to the cables 56a is maintained so that the lower portion of the moving element 65A is disposed inside a clearance formed by the extending portions 38a and 38b. Further, the moving lens unit 32 is held at a position thereof after the aforementioned control has been performed, by an urging force of the leaf spring 64. Therefore, for example, even if a disturbance occurs in response to a change in the ambient temperature around the distal end portion 21 after an instruction at the tele switch 29a stops, the position of the moving lens frame 38 does not fluctuate.

Figure 18:
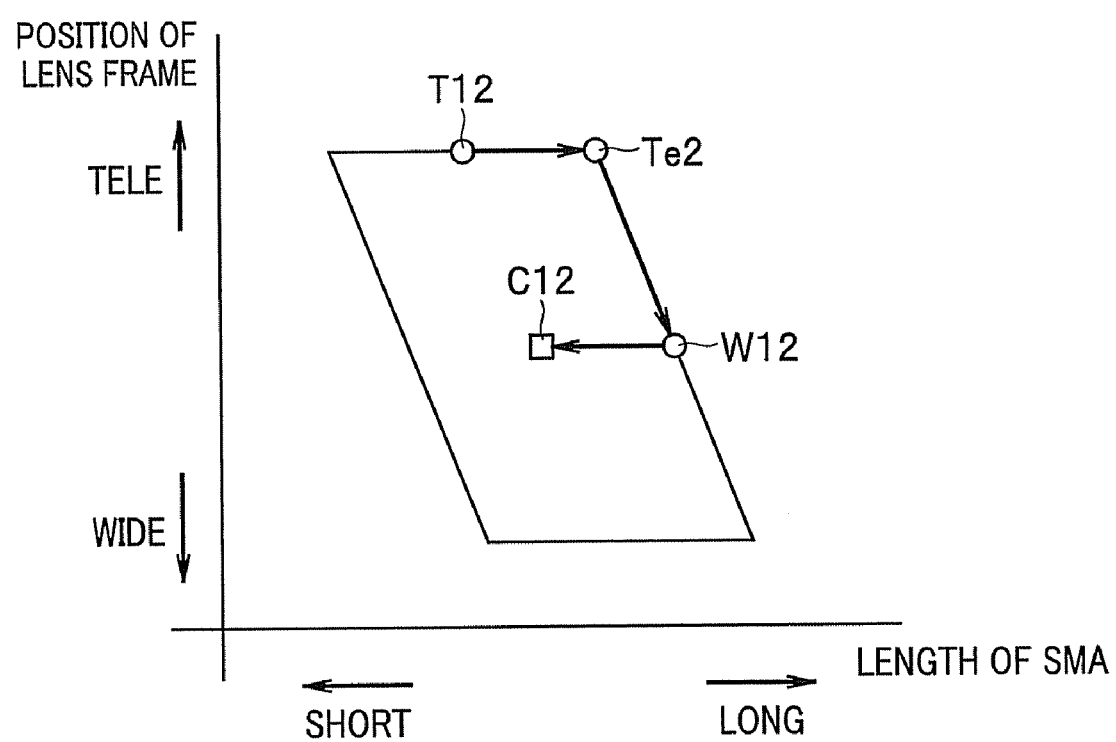
FIG. 18 is a view that illustrates a manner in which a length of the SMA wire and a position of the moving lens frame change when control of the second embodiment is performed in accordance with a wide-photographing instruction.
Figure 19:
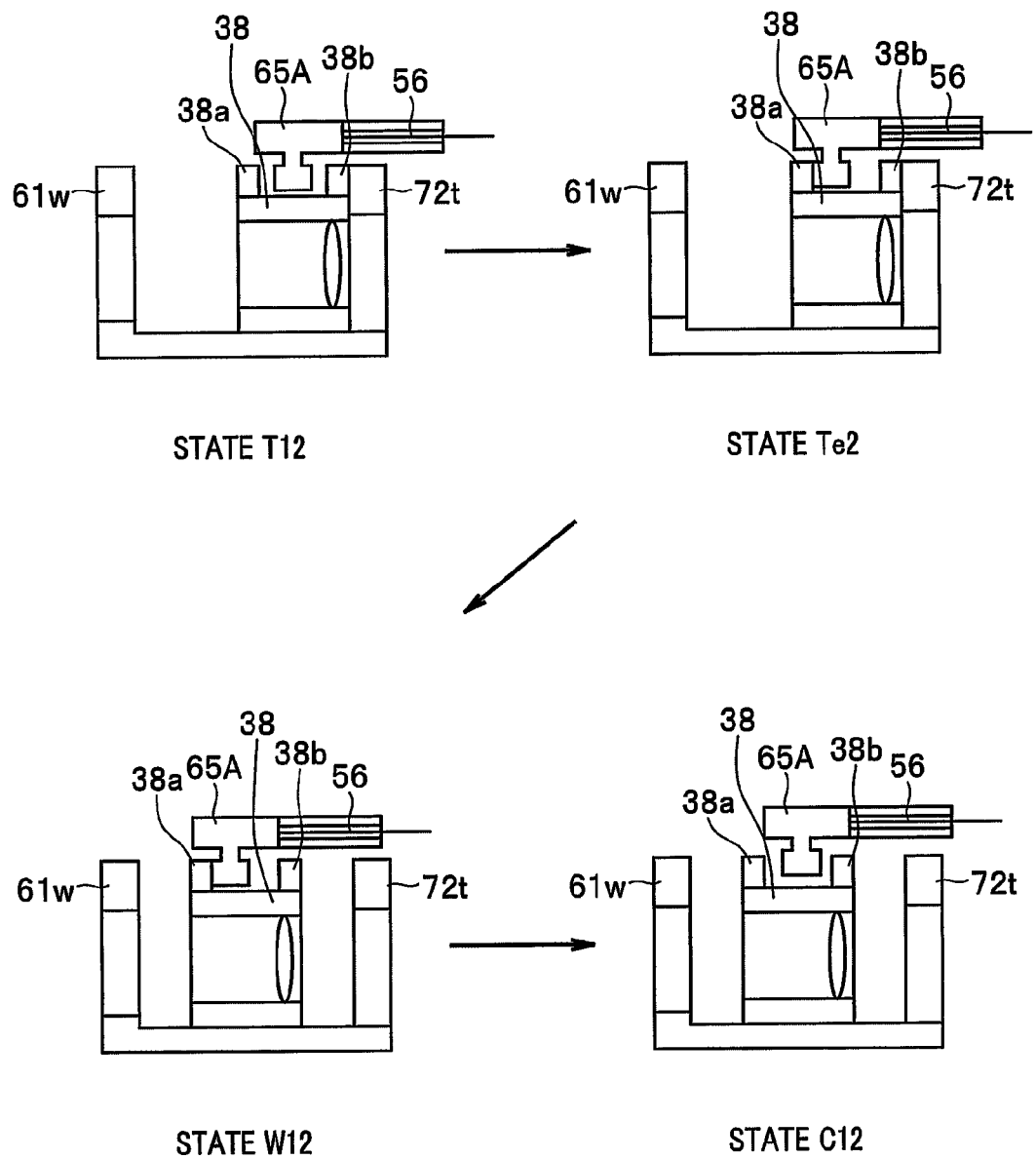
FIG. 19 is a view that illustrates a manner in which the moving element and the moving lens frame move in response to the control illustrated in FIG. 18.

Meanwhile, for example, when the moving lens frame 38 is at a furthest position on the tele side, the wire control portion 4a maintains an applied voltage to the cables 56a so as to enter a state T12 shown in FIG. 18 and FIG. 19.

The state T12 shown in FIG. 18 and FIG. 19 is a state in which the rear face portion of the extending portion 38b and the front face portion of the regulating portion 72t are in contact, and the moving element 65A is not in contact with either of the extending portions 38a and 38b. That is, in the state T12 shown in FIG. 18 and FIG. 19, the moving element 65A is disposed at a position that is separated from the moving lens frame 38 along the optical axis O direction.

Upon detecting that an instruction has been made at the wide switch 29b when in the state T12, the wire control portion 4a reduces the temperature of the SMA wire 56 by performing control to decrease the applied voltage to the cables 56a. The wire control portion 4a continues the control to decrease the applied voltage to the cables 56a while the instruction at the wide switch 29b is continuing.

When the applied voltage to the cables 56a continues to be decreased, the amount of deformation of the SMA wire 56 gradually increases as a result of the decrease in the temperature of the SMA wire 56, and thus the SMA wire 56 relaxes and lengthens. As a result of the lengthening of the SMA wire 56, the moving lens frame 38 that is in the state Te2 begins to slide to the wide side.

Thereafter, upon detecting that the instruction at the wide switch 29b has stopped, the wire control portion 4a performs control to increase the applied voltage to the cables 56a by a predetermined amount from the applied voltage at the time that the instruction stopped, and to maintain the applied voltage at the increased amount.

More specifically, for example, when the aforementioned control is performed in a state W12 shown in FIG. 18 and FIG. 19, the temperature of the SMA wire 56 increases in accordance with the amount of increase in the applied voltage to the cables 56a. Accompanying this increase in temperature, the length of the SMA wire 56 and the position of the moving lens frame 38 change from the state W12 to a state C12 shown in FIG. 18 and FIG. 19.

The state C12 shown in FIG. 18 and FIG. 19 is a state in which the moving lens frame 38 is positioned approximately midway between the tele side and the wide side, the front face portion of the extending portion 38a and the rear face portion of the regulating portion 61w are not in contact, the rear face portion of the extending portion 38b and the front face portion of the regulating portion 72t are not in contact, and the moving element 65A is not in contact with either of the extending portions 38a and 38b. That is, in the state C12 shown in FIG. 18 and FIG. 19, the moving element 65A is disposed at a position that is separated from the moving lens frame 38 along the optical axis O direction.

According to the above described control, an applied voltage to the cables 56a is maintained so that the lower portion of the moving element 65A is disposed inside a clearance formed by the extending portions 38a and 38b. Further, the moving lens unit 32 is held at a position thereof after the aforementioned control has been performed, by an urging force of the leaf spring 64. Therefore, for example, even if a disturbance occurs in response to a change in the ambient temperature around the distal end portion 21 after an instruction at the wide switch 29b stops, the position of the moving lens frame 38 does not fluctuate.

Figure 20:
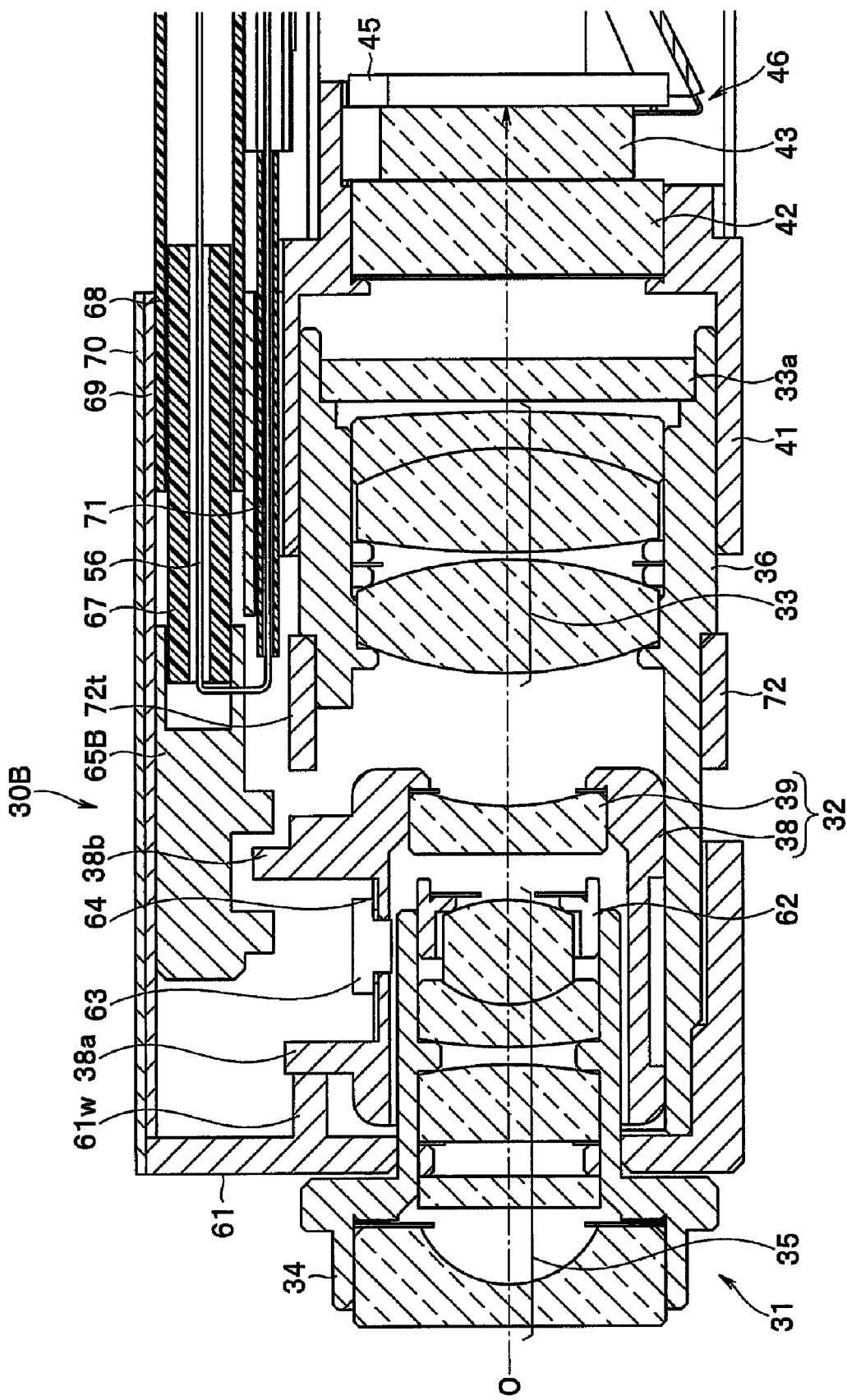
FIG. 20 is a sectional view that illustrates an example of the internal configuration of the image pickup unit according to the second embodiment that is different to the example shown in FIG. 12.
Figure 21:
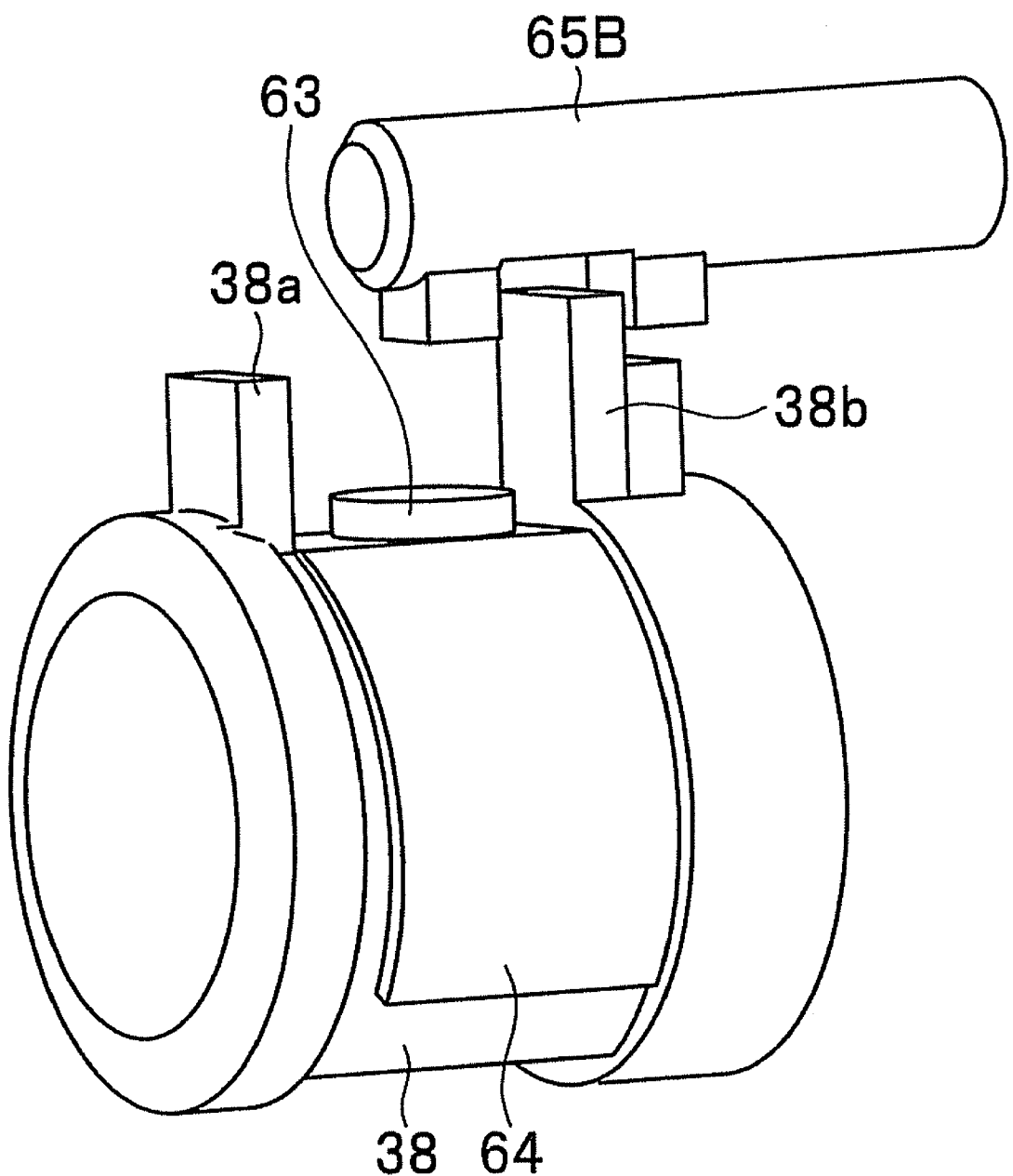
FIG. 21 is a perspective view that illustrates an example of the configuration of the moving element and the moving lens frame according to the second embodiment that is different to the example shown in FIG. 13.
Figure 22:
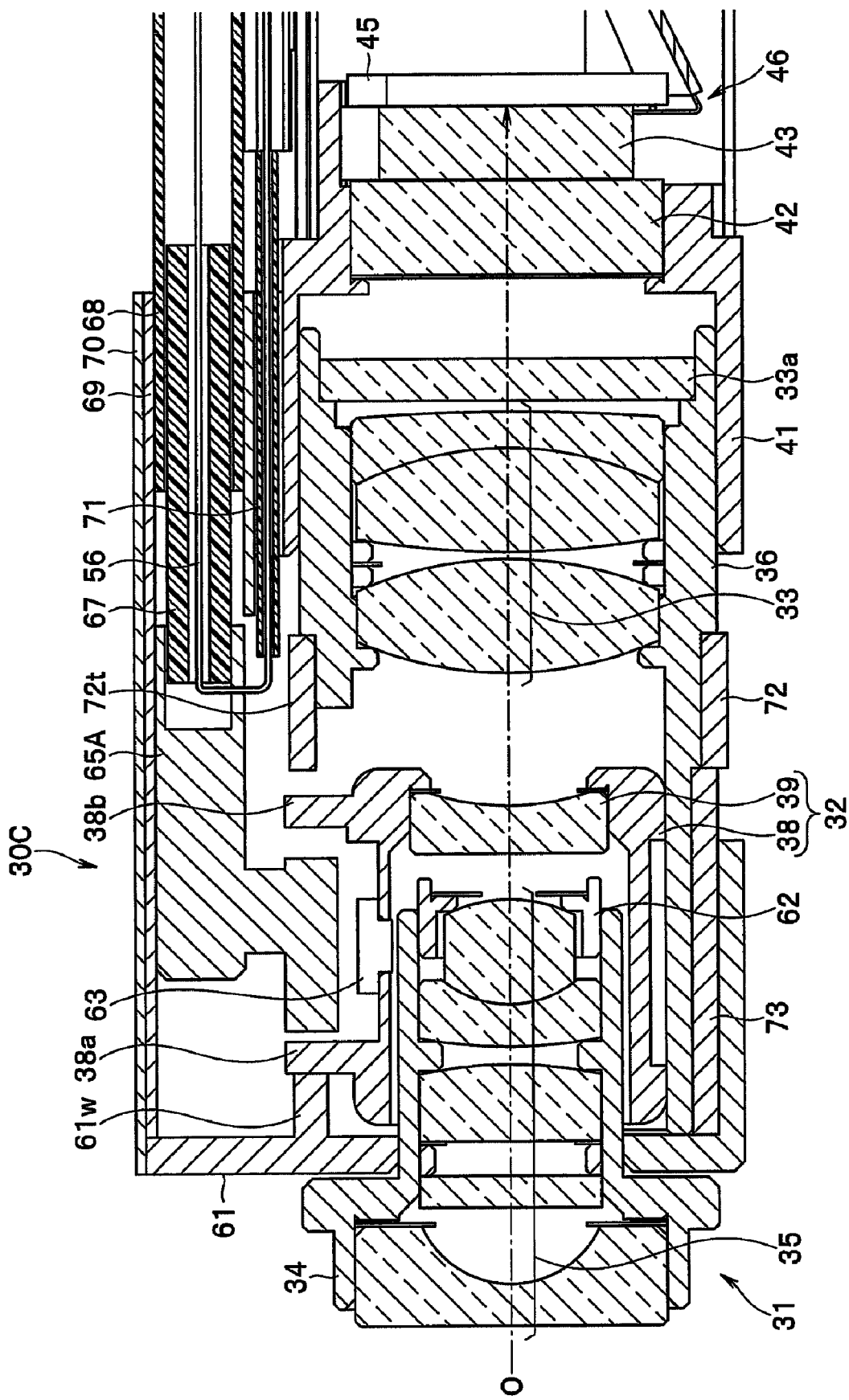
FIG. 22 is a sectional view that illustrates an example of the internal configuration of the image pickup unit according to the second embodiment that is different to the examples shown in FIG. 12 and FIG. 20.

In this connection, the control of the present embodiment is not limited to control that is applied to the image pickup unit 30A in which the lower portion of the moving element 65A is disposed in a clearance formed by the extending portions 38a and 38b. For example, as shown in FIG. 20 and FIG. 21, the control of the present embodiment is also applicable to an image pickup unit 30B in which at least one part of the extending portion 38b is disposed inside a clearance that is formed by an inverted concave portion of a moving element 65B.

According to the configuration and actions of the present embodiment described above, even when a change in the ambient temperature around the distal end portion 21 of the endoscope 2 acts as a disturbance, the moving element 65A runs freely inside a clearance formed by the extending portions 38a and 38b, and the moving lens frame 38 does not move. It is thus possible to prevent movement of the moving lens 39 to a position to which movement thereof is originally not intended.

Further, according to the configuration and actions of the present embodiment described above, even in a case where the moving element 65A moves with respect to the distal end portion 21 of the endoscope 2 due to a change in the relative positions of the SMA wire 56 and the tube member 67 and guide pipe 68 through which the SMA wire 56 is inserted that occurs in response to a bending operation of the bending portion 22, the moving element 65A runs freely inside a clearance formed by the extending portions 38a and 38b, and the moving lens frame 38 does not move. Hence, it is possible to prevent movement of the moving lens 39 to a position to which movement thereof is originally not intended.

Note that the present embodiment is not limited to a configuration in which the moving lens unit 32 is held by an urging force of the leaf spring 64, and a configuration may be adopted in which the moving lens unit 32 is held by a magnetic force emitted from a magnet. More specifically, the present embodiment is not limited to a configuration in which the leaf spring 64 whose upper portion is fixed by a screw 63 is provided in the moving lens frame 38. For example, as illustrated by an image pickup unit 30C shown in FIG. 22, a configuration may be adopted in which a magnet 73 is provided between the rear group lens frame 36 and the lens frame pressing member 61, and the moving lens frame 38 is formed using a magnetic body. Such a configuration of the image pickup unit 30C can also be applied in a substantially similar manner to the image pickup unit 30 of the first embodiment.

Meanwhile, according to the configuration and actions of the present embodiment, resistance to a disturbance that accompanies a change in the ambient temperature around the distal end portion 21 can be further strengthened by changing the respective applied voltages to the cables 56a in the aforementioned states W11, C11, T12 and C12 to a voltage such that a temperature of the SMA wire 56 becomes a temperature that belongs to the dead zone of the hysteresis characteristic of the SMA wire 56 shown in FIG. 8 and FIG. 10 and maintaining the changed voltages.

In this connection, generally, since there are many cases in which air or water is supplied to a diseased part when performing in-vivo observation or the like using an endoscope, an ambient temperature around a distal end portion of the endoscope is liable to change. This means that a cause of a disturbance is liable to arise in a case where a moving lens unit provided at the distal end portion of the endoscope is moved using an SMA wire.

Further, an ordinary endoscope is configured so that a movable range in an optical axis direction of a moving lens unit is approximately 1 mm, and so as to optically switch between tele photographing and wide photographing by movement of the moving lens unit within the movable range. Therefore, when a change in an ambient temperature of a distal end portion of an endoscope acts as a disturbance on an SMA wire, even if the disturbance is a minute disturbance, a situation can arise in which, for example, an image of a diseased part is difficult to see due to movement of the moving lens unit.

That is, the effects described in the first embodiment and second embodiment can be exerted to a particularly noticeable degree in an endoscope that has a configuration in which a moving lens unit is moved using an SMA wire.

Note that the present invention is not limited to each of the embodiments described above, and naturally various modifications and applications are possible within a range that does not depart from the spirit or scope of the invention.

What is claimed is:

1. A lens drive control apparatus that controls a lens drive system that has a lens frame that holds a lens so as to be movable forward and backward in an optical axis direction of an optical lens, and a transmitting member that transmits to the lens frame a driving force generated by a strain deformation of a shape memory alloy member that exhibits a predetermined hysteresis characteristic between a temperature and an amount of deformation, comprising:
 a control section that, at a timing at which an instruction that causes the lens frame to move forward or backward stops, performs control that changes a temperature of the shape memory alloy member to a temperature belonging to a dead zone of the predetermined hysteresis characteristic, thereby preventing a position of the lens frame from fluctuating, wherein:
 while the instruction is continuing, the control section performs control that changes the temperature of the shape memory alloy member by continuing to change an applied voltage to the shape memory alloy member in an increasing/decreasing direction in accordance with the instruction, and
 at a timing at which the instruction stops, the control section performs control that changes the temperature of the shape memory alloy member to a temperature belonging to a dead zone of predetermined hysteresis characteristic by changing in the applied voltage to the shape memory alloy member by a predetermined amount in an opposite direction to the increasing/decreasing direction in which the applied voltage is changed while the instruction is continuing, and maintaining the applied voltage that is changed.

2. A lens drive apparatus comprising:
 a lens frame that holds a lens so as to be movable forward and backward in an optical axis direction of an optical lens;
 a shape memory alloy member;
 a transmitting member that is provided with a clearance along the optical axis direction with respect to the lens frame, and that transmits a driving force generated by a strain deformation of the shape memory alloy member to the lens frame; and
 a control section that, at a timing at which an instruction that causes the lens frame to move forward or backward stops, performs control that moves the transmitting member to a position that is separated from the lens frame along the optical axis direction, thereby preventing a position of the lens frame from fluctuating, wherein:
 the control section performs control that moves the transmitting member to a position that is inside the clearance and separated from the lens frame along the optical axis direction by:
 while the instruction is continuing, moving the lens frame and the transmitting Member forward or backward by continuing to change an applied voltage to the shape memory alloy member in an increasing/decreasing direction in accordance with the instruction, and
 at a timing at which the instruction stops, changing the applied voltage to the shape memory alloy member by a predetermined amount in an opposite direction to the increasing/decreasing direction thereof while the instruction is continuing, and maintaining the applied voltage that is changed.

3. The lens drive apparatus according to claim 2, further comprising a resistance force generating member that can generate a resistance force with respect to a movement of the lens frame that is caused by the weight of the lens frame.

4. A lens drive apparatus, comprising:
 a lens frame that holds a lens so as to be movable forward and backward in an optical axis direction of an optical lens;
 a transmitting member that is provided with a clearance along the optical axis direction with respect to the lens frame, and that transmits to the lens frame a driving force generated by a strain deformation of a shape memory alloy member that exhibits a predetermined hysteresis characteristic between a temperature and an amount of deformation; and
 a control section that, at a timing at which an instruction that causes the lens frame to move forward or backward stops, performs control that moves the transmitting member to a position that is separated from the lens frame along the optical axis direction, and changes a temperature of the shape memory alloy member to a temperature belonging to a dead zone of the predetermined hysteresis characteristic, thereby preventing a position of the lens frame from fluctuating, wherein:
 the control section performs control that moves the transmitting member to a position that is inside the clearance and separated from the lens frame along the optical axis direction by:
 while the instruction is continuing, moving the lens frame and the transmitting member forward or backward by continuing to change an applied voltage to the shape memory alloy member in an increasing/decreasing direction in accordance with the instruction, and
 at a timing at which the instruction stops, changing the applied voltage to the shape memory alloy member by a predetermined amount in an opposite direction to the increasing/decreasing direction thereof while the instruction is continuing, and maintaining the applied voltage that is changed.

5. An endoscope system, comprising:

an endoscope in which a lens frame that holds a lens so as to be movable forward and backward in an optical axis direction of an optical lens, and a transmitting member that is provided with a clearance along the optical axis direction with respect to the lens frame and that transmits to the lens frame a driving force generated by a strain deformation of a shape memory alloy member that exhibits a predetermined hysteresis characteristic between a temperature and an amount of deformation are provided in a distal end portion; and a control section that, at a timing at which an instruction that causes the lens frame to move forward or backward stops, performs control that moves the transmitting member to a position that is separated from the lens frame along the optical axis direction, and changes a temperature of the shape memory alloy member to a temperature belonging to a dead zone of the predetermined hysteresis characteristic, thereby preventing a position of the lens frame from fluctuating, wherein:

the control section performs control that moves the transmitting member to a position that is inside the clearance and separated from the lens frame along the optical axis direction by:

while the instruction is continuing, moving the lens frame and the transmitting member forward or backward by continuing to change an applied voltage to the shape memory alloy member in an increasing/decreasing direction in accordance with the instruction, and at a timing at which the instruction stops, changing the applied voltage to the shape memory alloy member by a predetermined amount in an opposite direction to the increasing/decreasing direction thereof while the instruction is continuing, and maintaining the applied voltage that is changed.

* * * * *